US012569532B2

(12) United States Patent
Koizumi et al.

(10) Patent No.: US 12,569,532 B2
(45) Date of Patent: Mar. 10, 2026

(54) BRAIN FUNCTION REGULATING AGENT, AND FOOD OR BEVERAGE PRODUCT CONTAINING SAME

(71) Applicant: NITTA GELATIN INC., Osaka (JP)

(72) Inventors: Seiko Koizumi, Yao (JP); Naoki Inoue, Yao (JP); Aya Matsushita, Yao (JP); Katsuyoshi Sunaga, Sakado (JP); Hidetomo Kikuchi, Sakado (JP); Satomi Kogure, Sakado (JP)

(73) Assignee: NITTA GELATIN INC., Osaka (JP)

( * ) Notice: Subject to any disclaimer, the term of this patent is extended or adjusted under 35 U.S.C. 154(b) by 218 days.

(21) Appl. No.: 17/946,098

(22) Filed: Sep. 16, 2022

(65) Prior Publication Data

US 2023/0016005 A1     Jan. 19, 2023

Related U.S. Application Data

(63) Continuation of application No. 17/274,705, filed as application No. PCT/JP2020/007806 on Feb. 26, 2020, now abandoned.

(30) Foreign Application Priority Data

Feb. 28, 2019     (JP) .............................. JP2019-036417

(51) Int. Cl.
*A61K 38/06* (2006.01)
*A23L 33/18* (2016.01)

(52) U.S. Cl.
CPC .............. *A61K 38/06* (2013.01); *A23L 33/18* (2016.08)

(58) Field of Classification Search
None
See application file for complete search history.

(56) References Cited

U.S. PATENT DOCUMENTS

| | | | | |
|---|---|---|---|---|
| 9,061,003 B2* | 6/2015 | Sugihara | .............. | C07K 5/0606 |
| 2004/0242853 A1* | 12/2004 | Greig | ..................... | A61P 19/08 |
| | | | | 530/399 |
| 2013/0303448 A1* | 11/2013 | Sugihara | ................. | A61P 43/00 |
| | | | | 514/6.9 |
| 2015/0182580 A1 | 7/2015 | Taga et al. | | |

FOREIGN PATENT DOCUMENTS

| | | | |
|---|---|---|---|
| CN | 103347530 | A | 10/2013 |
| CN | 104540960 | A | 4/2015 |
| CN | 107789216 | A | 3/2018 |
| JP | 4433082 | B1 | 3/2010 |
| JP | 2010-090129 | A | 4/2010 |
| JP | 2010-105996 | A | 5/2010 |
| JP | 2011-111440 | A | 6/2011 |
| JP | 2014-141450 | A | 8/2014 |
| JP | 2015-59087 | A | 3/2015 |
| JP | 2017-527537 | A | 9/2017 |
| JP | 2019-501181 | A | 1/2019 |
| WO | 2012/102308 | A1 | 8/2012 |
| WO | 2018/074791 | A1 | 4/2018 |

OTHER PUBLICATIONS

Koizumi, Seiko, et al. "Effects of collagen hydrolysates on human brain structure and cognitive function: a pilot clinical study." Nutrients 12.1 (U.S. Appl. No. 12/232,019): 50).*

Chinese Office Action dated Feb. 2, 2024 in Application No. 202080006421.9.

Tomoya Kitakaze, et al. "The collagen derived dipeptide hydroxyprolyl-glycine promotes C2C12 myoblast differentiation and myotube hypertrophy", Biochemical and Biophysical Research Communications, 2016, vol. 478, pp. 1292-1297 (6 pages).

Pei Xinrong, et al., "Preventive Effect of Marine Collagen Peptide on Learning and Memory Impairment in SAMP8 Mice", Food and Fermentation Industries, 2009, pp. 1-5, vol. 135, No. 07.

Akitoshi Nagai, et al., "Identification of Antidepressant Collagen Peptide and the Penetration into Cerebrospinal Fluid", Proceedings of 2017 Annual Meeting of Japan Society for Bioscience, Biotechnology and Agrochemistry, Mar. 5, 2017, p. 997.

Chikako Kakoi, et al., "Collagen peptides enhance hippocampal neurogenesis and reduce anxiety-related behavior in mice", Biomedical Research, 2012, pp. 273-279, vol. 33, No. 5.

International Search Report for PCT/JP2020/007806 dated May 26, 2020 [PCT/ISA/210].

Written Opinion for PCT/JP2020/007806 dated May 26, 2020 [PCT/ISA/237].

Japanese Office Action dated May 28, 2024 in Application No. 2021-502332.

Communication dated Oct. 1, 2024 in Chinese Application No. 202080006421.9.

* cited by examiner

*Primary Examiner* — Maury A Audet
(74) *Attorney, Agent, or Firm* — Sughrue Mion, PLLC

(57) ABSTRACT

A brain function regulating agent contains a peptide comprising an amino acid sequence represented by Glu-Hyp-Gly, a salt thereof, or a chemically modified product thereof.

2 Claims, 2 Drawing Sheets

BRAIN FUNCTION REGULATING AGENT, AND FOOD OR BEVERAGE PRODUCT CONTAINING SAME

CROSS REFERENCE TO RELATED APPLICATIONS

This application is a Continuation Applications of U.S. application Ser. No. 17/274,705, filed Mar. 9, 2021, which is a National Stage of International Application No. PCT/JP2020/007806 filed Feb. 26, 2020, claiming priority based on Japanese Patent Application No. 2019-036417 filed Feb. 28, 2019, the entire contents of which are hereby incorporated by reference.

TECHNICAL FIELD

The present invention relates to a brain function regulating agent, and a food or beverage product containing the same.

BACKGROUND ART

Collagen hydrolysates (hereinafter, also referred to as "collagen peptide mixtures") are known to exhibit various physiological activities on living organisms. Recently, it has come to be reported that collagen peptide mixtures exhibit physiological activities on cerebral nerve cells, and the like, and have an improving effect on brain functions such as a memory (hereinafter, also referred to as a "brain function improving effect"). For example, Japanese Patent Laying-Open No. 2010-105996 (PTL 1) discloses a neurogenesis promoter containing a total of nine collagen-derived peptides including a peptide represented by Gly-Pro-Arg. Japanese Patent Laying-Open No. 2011-111440 (PTL 2) discloses that a peptide derived from collagen and represented by Gly-Pro-Ala has a neurogenesis promoting action. NPL 1 reports that administration of a fish-derived collagen peptide mixture to an aged model mouse increases the expression level of BDNF (brain-derived neurotrophic factor) in the hippocampus, resulting in enhancement of the spatial learning memory ability and the passive avoidance ability. NPL 2 reports that in an experiment using rats, a collagen-derived dipeptide represented by Pro-Hyp exhibited an antidepressant effect when transferred into the cerebrospinal fluid. NPL 3 reports that a collagen hydrolysate promoted neurogenesis in the hippocampus.

CITATION LIST

Patent Literature

PTL 1: Japanese Patent Laying-Open No. 2010-105996
PTL 2: Japanese Patent Laying-Open No. 2011-111440

Non Patent Literature

NPL 1: Pei Xinrong et al., "Preventive Effect of Marine Collagen Peptide on Learning and Memory Impairment in SAMP8 Mice", Food and Fermentation Industries, 2009, Vol 135(07), p. 1-5
NPL 2: Nagai et al., "Identification of Antidepressant Collagen Peptide and the Penetration into Cerebrospinal Fluid", Proceedings of 2017 Annual Meeting of Japan Society for Bioscience, Biotechnology, and Agrochemistry, 5 Mar. 2017, p. 997

NPL 3: C. Kakoi et al., "Collagen peptides enhance hippocampal neurogenesis and reduce anxiety related behavior in mice", Biomedical Research 33(5), 2012, p. 273-279

SUMMARY OF INVENTION

Technical Problem

NPL 1 and NPL 3 do not specify what collagen-derived peptides produce the disclosed brain function improving effect or neurogenetic action. PTL 1 does not specify which of the nine collagen-derived peptides have the disclosed neurogenesis promoting action. The neurogenesis promoting action disclosed in PTL 2 is a finding obtained from an experiment using PC12 cells derived from a rat adrenal pheochromocytoma, and is not a finding obtained from an experiment targeting cerebral nerve cells. Further, the Pro-Hyp disclosed in NPL 2 is suggested to have a neurogenetic action in the hippocampal dentate gyrus, but it is not confirmed whether Pro-Hyp differentiates and grows cerebral nerve cells to improve the brain function. Therefore, a collagen-derived peptide has not been known yet which produces a brain function improving effect by directly acting on cerebral nerve cells without signal transducers in the body such as a hormone, and development of such a peptide is desired.

In view of the above-described circumstances, an object of the present invention is to provide a brain function regulating agent comprising a peptide etc. which produces at least one of a brain function improving effect and a brain function decline preventing effect by directly acting on cerebral nerve cells, and a food or beverage product containing the brain function regulating agent.

Solution to Problem

In development of a brain function regulating agent comprising a peptide etc. which produces at least one of a brain function improving effect and a brain function decline preventing effect by directly acting on cerebral nerve cells, the present inventors have focused on Glu-Hyp-Gly (glutamic acid-hydroxyproline-glycine, which may be hereinafter referred to as "EOG" that is an abbreviation in which each amino acid is represented by one character) among amino acid sequences of peptides contained in a collagen peptide mixture. The present inventors have found that when acting on cerebral nerve cells, the collagen peptide mixture containing a peptide comprising an amino acid sequence represented by Glu-Hyp-Gly, specifically a tripeptide represented by Glu-Hyp-Gly, etc., promotes differentiation of cerebral nerve cells, thereby producing a brain function improving effect and a brain function decline preventing effect, and thus the present invention has been achieved. Specifically, the present invention is as follows.

A brain function regulating agent according to the present invention comprises a peptide comprising an amino acid sequence represented by Glu-Hyp-Gly, a salt thereof, or a chemically modified product thereof.

Preferably, the peptide, a salt thereof, or a chemically modified product thereof is a tripeptide represented by Glu-Hyp-Gly, a salt thereof, or a chemically modified product thereof.

Preferably, the peptide is derived from collagen.

Preferably, the peptide has a weight average molecular weight of 315 or more and 10,000 or less.

Preferably, the brain function regulating agent is a brain function improving agent or a brain function decline preventing agent.

Preferably, the brain function regulating agent has a cerebral nerve cell differentiation promoting action.

Preferably, the brain function regulating agent has a cerebral nerve cell death suppressive action.

Preferably the brain function regulating agent has a memory or cognitive function improving action.

A food or beverage product according to the present invention comprises the brain function regulating agent.

Advantageous Effects of Invention

According to the present invention, it is possible to provide a brain function regulating agent comprising a peptide etc. which produces at least one of a brain function improving effect and a brain function decline preventing effect by directly acting on cerebral nerve cells, and a food or beverage product comprising the brain function regulating agent.

DESCRIPTION OF EMBODIMENTS

Figure 1:
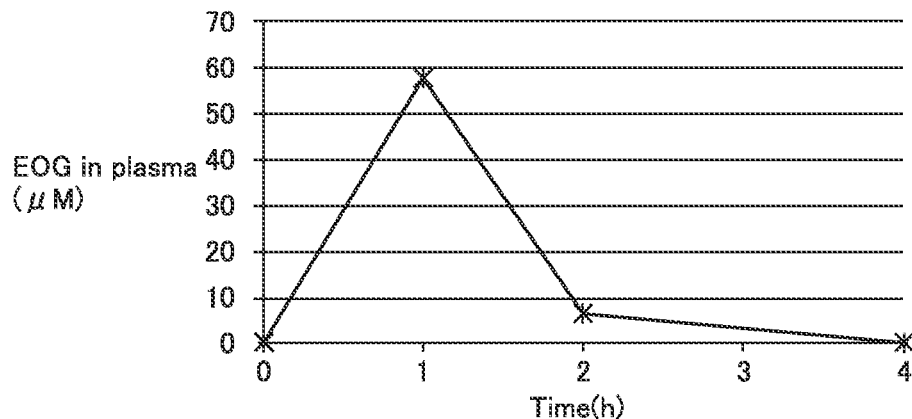
FIG. 1 is a graph showing the amount of EOG in the plasma (sample a) of male mice after the elapse of a predetermined period of time after gavage administration of EOG to the male mice.

Hereinafter, embodiments of the present invention will be described in more detail. As used herein, the notation in the form of "A to B" means the upper limit and the lower limit of a range (i.e. A or more and B or less), and when a unit is not described for A, and a unit is described only for B, the unit for A is identical to the unit for B.

[Brain Function Regulating Agent]

A brain function regulating agent according to the present invention contains a peptide comprising an amino acid sequence represented by Glu-Hyp-Gly, a salt thereof, or a chemically modified product thereof. The brain function regulating agent having such a characteristic can promote differentiation of cerebral nerve cells by directly acting on cerebral nerve cells, thereby producing a brain function improving effect and a brain function decline preventing effect.

<Peptide Comprising Amino Acid Sequence Represented by Glu-Hyp-Gly, Salt Thereof, or Chemically Modified Product Thereof>

As described above, the brain function regulating agent comprises a peptide comprising an amino acid sequence represented by Glu-Hyp-Gly, a salt thereof, or a chemically modified product. The term "amino acid" as used herein means an "L-amino acid", unless otherwise specified. The term "peptide comprising an amino acid sequence represented by Glu-Hyp-Gly" means that an amino acid sequence constituting such a peptide comprises one or more amino acid sequences represented by "Glu-Hyp-Gly (glutamic acid-hydroxyproline-glycine)".

In the brain function regulating agent, the peptide, a salt thereof, or a chemically modified product thereof is preferably a tripeptide represented by Glu-Hyp-Gly, a salt thereof, or a chemically modified product thereof. Here, the brain function regulating agent can more markedly exert a cerebral nerve cell differentiation promoting action.

The term "salt" of the peptide can be formed as, for example, an inorganic acid salt such as a hydrochloride, a sulfate or a phosphate, an organic acid salt such as a methanesulfonate salt, a benzenesulfonate salt, a succinate salt or an oxalate salt, an inorganic basic salt such as a sodium salt, a potassium salt or a calcium salt, an organic basic salt such as a triethylammonium salt.

The term "chemically modified product" of the peptide is a peptide in which a free functional group of an amino acid residue as a constitutional unit is chemically modified. Chemical modification can be performed on, for example, a hydroxyl group of hydroxyproline, an amino group of an amino acid on the N-terminal (amino terminal) side and a carboxyl group of an amino acid on the C-terminal (carboxyl terminal) side. Specific means and treatment conditions for chemical modification follow known conventional techniques for chemical modification of peptides. The chemically modified product of the peptide, which is obtained by such chemical modification, can produce an enhancing effect on solubility under a mildly acidic to neutral condition, an enhancing effect on compatibility with other active ingredients, and the like.

For example, the tripeptide of Glu-Hyp-Gly can be subjected to O-acetylation as chemical modification of a hydroxyl group in hydroxyproline. The O-acetylation can be performed by applying acetic anhydride to the peptide in an aqueous solvent or a nonaqueous solvent. Esterification, amidation or the like can be performed as chemical modification of a carboxyl group in glycine. The esterification can be performed by suspending the peptide in methanol, and then causing dry hydrogen chloride gas to pass through the resulting suspension. The amidation can be performed by applying carbodiimide or the like to the peptide.

Methylation can be performed as chemical modification of a free amino group in the tripeptide. At least one of phosphorylation and sulfation can be performed as chemical modification of a hydroxyl group in the tripeptide.

Preferably, the peptide is derived from collagen. Here, the collagen as a raw material can be obtained by performing known conventional defatting or decalcification treatment, extraction treatment or the like on, for example, the skin, the dermis, the bone, the cartilage, the tendon or the like of animals typically of a bovine, a pig, a sheep, a chicken or an ostrich, or the bone, the skin, the scale or the like of fish. Further, gelatin can be used as a raw material for the peptide. The gelatin can be obtained by treating the thus-obtained collagen through a known conventional method such as extraction with hot water. For the collagen and the gelatin, commercial products can be used as raw materials.

The peptide can be obtained by hydrolyzing the collagen and/or the gelatin with two or more of endo-type proteases and exo-type proteases in combination. The peptide can be obtained as a collagen peptide mixture which exists together with other collagen peptides due to the hydrolysis, but any of the collagen peptide mixture itself and a mixture obtained by partially purifying the collagen peptide mixture can be used as the brain function regulating agent according to the present invention. By further purifying the collagen peptide mixture, a peptide comprising an amino acid sequence represented by Glu-Hyp-Gly can be obtained with a high purity. When the peptide is derived from collagen, it is preferable to obtain the peptide by using a method in which collagen or gelatin is enzyme-treated in two stages as described below.

Further, the peptide preferably has a weight average molecular weight of 315 or more and 10,000 or less. The weight average molecular weight of the peptide is more preferably 315 or more and 5,000 or less, still more preferably 315 or more and 2,000 or less. When the weight average molecular weight of the peptide is within the above-described range, the brain function regulating agent more markedly exert the cerebral nerve cell differentiation promoting action, thereby producing a more sufficient brain function improving effect and brain function decline preventing effect. When the weight average molecular weight of the peptide is more than 10,000, the brain function regulating agent may have an insufficient brain function improving effect and brain function decline preventing effect.

The weight average molecular weight of the peptide can be determined by carrying out size exclusion chromatography (SEC) under the following measurement conditions.

Equipment: High-performance liquid chromatography (HPLC) (manufactured by TOSOH CORPORATION)
Column: TSKGel (registered trademark) G2000SW$_{XL}$
Column temperature: 40° C.
Eluant: 45 mass % acetonitrile (with 0.1 mass % TFA)
Flow rate: 1.0 mL/min
Injection amount: 10 μL
Detection: UV 214 nm
Molecular weight marker: The following five types are used

| Cytochrome C | Mw: 12,000 |
| Aprotinin | Mw: 6,500 |
| Bacitracin | Mw: 1,450 |
| Gly-Gly-Tyr-Arg | Mw: 451 |
| Gly-Gly-Gly | Mw: 189 |

Specifically, a sample containing about 0.2 g of the peptide (collagen peptide mixture) is added to about 100 ml of distilled water, and the mixture is stirred, and then filtered with a 0.2 μm filter to prepare a sample of which weight average molecular weight is measured (measurement specimen). By subjecting the measurement speciment to the size exclusion chromatography, the weight average molecular weight of the peptide can be determined. When the peptide is a tripeptide represented by Glu-Hyp-Gly, the molecular mass thereof can be the weight average molecular weight.

<Method for Producing Brain Function Regulating Agent>

The peptide contained in the brain function regulating agent and including comprising an amino acid sequence represented by Glu-Hyp-Gly can be obtained by using a known conventional liquid-phase or solid-phase peptide synthesis method, or a method including hydrolyzing collagen or gelatin. For example, from the viewpoint of efficiency, it is preferable to produce the peptide by using a chemical synthesis method using an amino acid as described below, or a method including enzymatically treating collagen or gelatin in two stages as described below. Further, the peptide can be produced by using a method including performing enzymatic treatment with only a secondary enzyme with a primary enzyme omitted, or a method including performing enzymatic treatment with a primary enzyme and a secondary enzyme simultaneously, instead of the method including enzymatically treating collagen or gelatin in two stages.

(Chemical Synthesis Method)

The peptide can be obtained by using a common peptide synthesis method. As the peptide synthesis method, a solid-phase synthesis method and a liquid-phase synthesis method are known. As the solid-phase synthesis method, an Fmoc method and a Boc method are known. The peptide can be obtained by using either of the Fmoc method and the Boc method. Hereinafter, a method for synthesizing a tripeptide represented by, for example, Glu-Hyp-Gly will be described as the solid-phase peptide synthesis method.

First, a bead of a polystyrene polymer gel having a diameter of about 0.1 mm and having a surface modified with amino groups is provided as a solid phase. Separately, diisopropylcarbodiimide is provided as a condensing agent. Next, the amino group of glycine, which is an amino group on the C-terminal (carboxyl terminal) side in the amino acid sequence, is protected with an Fmoc (fluorenyl-methoxy-carbonyl) group, the carboxyl group of the glycine is peptide-bound to the amino group as the solid phase through a dehydration reaction using the condensing agent. Further, the solid phase is washed with a solvent to remove the remaining condensing agent and amino acids, followed by removing the protecting group (deprotecting) of the amino group of glycine which is peptide-bound to the solid phase.

Subsequently, hydroxyproline in which an amino group is protected with an Fmoc group is provided, and the carboxyl group of the hydroxyproline is peptide-bound to the deprotected amino group of the glycine by using the condensing agent. Thereafter, in the same manner as described above, the amino group of the hydroxyproline is deprotected, glutamic acid protected with an Fmoc group is provided, and a reaction for peptide-binding the glutamic acid to the hydroxyproline is carried out to synthesize a tripeptide represented by Glu-Hyp-Gly on the solid phase. Finally, the amino group of the glutamic acid is deprotected, a solution containing trifluoroacetic acid is added at room temperature, and the mixture is shaken for a fixed period of time to separate the tripeptide from the solid phase. This enables production of the tripeptide.

(Production Method Using Collagen and Gelatin)

Hereinafter, a method for producing a tripeptide represented by Glu-Hyp-Gly (hereinafter, also referred to as "specific peptide") by enzymatically treating collagen or gelatin in two stages will be described as an example of a method for producing the peptide.

The term "enzymatically treating (collagen or gelatin) in two stages" means the following. That is, primary enzymatic treatment is performed by a known conventional method for breaking the peptide bond of collagen or gelatin, and secondary enzymatic treatment is then performed with an enzyme having aminopeptidase N activity, an enzyme having both aminopeptidase N activity and prolyl tripeptidyl aminopeptidase activity, or a combination of an enzyme having aminopeptidase N activity and an enzyme having prolyl tripeptidyl aminopeptidase activity. By performing the primary enzymatic treatment, a collagen peptide mixture precursor can be obtained. By further performing the secondary enzymatic treatment, a collagen peptide mixture containing the specific peptide can be obtained from the collagen peptide mixture precursor. The method for enzymatically treating collagen or gelatin in two stages will be described in more detail below.

—Primary Enzymatic Treatment—

The enzyme used in the primary enzymatic treatment should not be particularly limited as long as it is an enzyme capable of breaking peptide bonds of collagen or gelatin, and any proteolytic enzyme can be used. Specifically, examples of thereof include collagenase, thiol protease, serine protease, acidic protease, alkaline protease and metal protease. One selected from the group consisting of these enzymes may be used alone, or two or more thereof may be used in combination. As the thiol protease, chymopapain, papain, bromelain and ficin derived from plants, cathepsin and calcium dependent protease derived from animals, and the like can be used. As the serine protease, trypsin, cathepsin D and the like can be used. As the acidic protease, pepsin, chymotrypsin and the like can be used. Considering that the brain function regulating agent is used for medicaments, specified health food and the like, it is preferable that as the enzymes used in the primary enzymatic treatment, those other than enzymes derived from pathogenic microorganisms be used.

The amount of enzymes in the primary enzymatic treatment is, for example, preferably 0.1 to 5 parts by mass of the above-described enzymes based on 100 parts by mass of collagen or gelatin. Preferably, the treatment temperature and the treatment time in the primary enzymatic treatment are 30 to 65° C. and 10 minutes to 72 hours, respectively. The weight average molecular weight of the collagen peptide mixture precursor obtained through the primary enzymatic treatment is preferably 500 to 10,000, more preferably 500 to 5,000, still more preferably 500 to 2,000. It can be said that when the weight average molecular weight is within the above-described range, a peptide having an appropriate molecular weight is adequately generated. If necessary, the enzyme can be deactivated after the primary enzymatic treatment. In this case, the deactivation temperature is, for example, preferably 70 to 100° C. The weight average molecular weight of the collagen peptide mixture precursor can be determined by the method using SEC.

—Secondary Enzymatic Treatment—

Examples of the enzyme used in the secondary enzymatic treatment include enzymes having aminopeptidase N activity, enzymes having both aminopeptidase N activity and prolyl tripeptidyl aminopeptidase activity, and combinations of an enzyme having aminopeptidase N activity and prolyl tripeptidyl aminopeptidase activity. The term "enzyme having aminopeptidase N activity" as used herein is a peptidase having a function of releasing an amino acid from the N-terminal side of the peptide chain, where the enzyme acts when an amino acid other than proline or hydroxyproline exists at the second position from the N-terminal side. The term "enzyme having prolyl tripeptidyl aminopeptidase activity" as used herein is a peptidase which releases only three amino acid residues on the N-terminal side from a peptide having proline or hydroxyproline at the third position from the N-terminal side. Considering that the brain function regulating agent is used for medicaments, specified health food and the like, it is preferable that as the enzymes used in the secondary enzymatic treatment, those other than enzymes derived from pathogenic microorganisms be used.

Examples of the enzyme having aminopeptidase N activity include aminopeptidase N (EC 3.4.11.2.; T. Yoshimoto et al., Agric. Biol. Chem., 52: 217-225 (1988)), and enzymes having aminopeptidase N activity derived from *Aspergillus*. Examples of the enzyme having prolyl tripeptidyl aminopeptidase activity include prolyl tripeptidyl aminopeptidase (EC 3.4.14.; A. Banbula et al., J. Biol. Chem., 274: 9246-9252 (1999)).

By performing the secondary enzymatic treatment, a collagen peptide mixture containing a peptide which has not been contained in the collagen peptide mixture precursor can be obtained. Specifically, a collagen peptide mixture containing the specific peptide can be obtained.

The amount of enzymes in the secondary enzymatic treatment is, for example, preferably 0.01 to 5 parts by mass of the above-described enzymes based on 100 parts by mass of the collagen peptide mixture precursor. Preferably, the treatment temperature and the treatment time in the secondary enzymatic treatment are 30 to 65° C. and 1 to 72 hours, respectively. The weight average molecular weight of the collagen peptide mixture obtained through the secondary enzymatic treatment is preferably 315 to 10,000, more preferably 315 to 5,000, still more preferably 315 to 2,000. The weight average molecular weight of the collagen peptide mixture can be determined by the method using SEC.

The secondary enzymatic treatment is performed mainly for the purpose of generating the specific peptide. Thus, it is preferable to adjust the amount of enzymes, the treatment temperature, the treatment time and the pH in the secondary enzymatic treatment so that the peptide contained in the collagen peptide mixture precursor is not excessively hydrolyzed. Accordingly, the weight average molecular weight of the collagen peptide mixture is preferably within the above-described range. It is necessary to deactivate the enzyme after the secondary enzymatic treatment. In this case, the deactivation temperature is, for example, preferably 70 to 100° C. Further, it is preferable to perform sterilization treatment at 120° C. for several seconds or more. In addition, the collagen peptide mixture can be subjected to spray drying by applying heat at 200° C. or higher.

In the secondary enzymatic treatment, not only the enzymes having aminopeptidase N activity and enzymes having prolyl tripeptidyl aminopeptidase activity, but also enzymes having different activities can be used, and two or more enzymes each having different activities can be used in combination. Consequently, by-products can be digested and removed. Preferably, the enzymes used in this case are appropriately selected, depending on the type of collagen used as a raw material, and the type of enzyme used in the primary enzymatic treatment. Examples of the different activities include dipeptidase activity such as prolidase activity and hydroxyprolidase activity. Consequently, by-products such as dipeptides can be digested and removed.

Further, the aminopeptidase N activity is basically activity causing the release of amino acids on the N-terminal side one by one. Thus, when the secondary enzymatic treatment is performed only with an enzyme having aminopeptidase N activity in the case where the collagen peptide mixture precursor obtained through the primary enzymatic treatment contains a peptide having an extremely large molecular weight, the duration for the secondary enzymatic treatment markedly increases. For coping with such a case, for example, prolyl oligopeptidase which is an endopeptidase having activity causing hydrolysis of proline on the carboxyl group side (prolidase activity) can be used in the secondary enzymatic treatment. Consequently, the secondary enzymatic treatment can be efficiently performed.

In the method including enzyme-treating collagen or gelatin in two stages, the primary enzymatic treatment enables generation of a peptide having a relatively large molecular weight. This peptide can have an amino acid sequence represented by, for example, [$X_1$-Gly-$X_2$-Glu-Hyp-Gly] ($X_1$ and $X_2 \neq$ Hyp). In the subsequent secondary enzymatic treatment, an enzyme having aminopeptidase N activity acts on the peptide represented by [$X_1$-Gly-$X_2$-Glu- Hyp-Gly], so that $X_1$ at the N-terminal is released to obtain a peptide having an amino acid sequence represented by [Gly-$X_2$-Glu-Hyp-Gly]. Next, an enzyme having aminopeptidase N activity acts twice on the peptide represented by [Gly-$X_2$-Glu-Hyp-Gly], so that glycine and $X_2$ are released to obtain a peptide represented by [Glu-Hyp-Gly]. In this way, a specific peptide can be generated.

—Purification of Collagen Peptide Mixture—

By performing enzymatic treatment in two stages as described above, a collagen peptide mixture containing a specific peptide can be produced. Since the collagen peptide mixture contains peptides other than the specific peptide, i.e. peptides other than the tripeptide represented by Glu-Hyp-Gly, it is preferable to purify the collagen peptide mixture if necessary. As a purification method in this case, a known conventional method can be used, and examples thereof include ultrafiltration, and various types of liquid chromatography such as size exclusion chromatography, ion-exchange chromatography, reversed phase chromatography and affinity chromatography.

Specifically, the collagen peptide mixture can be purified in accordance with the following procedure. That is, about 2 g/10 ml of the collagen peptide mixture is loaded into an ion-exchange column (e.g. "TOYOPEARL" (registered trademark) DEAE-650" (trade name) manufactured by TOSOH CORPORATION), and a first void volume fraction eluted with distilled water is then collected. Subsequently, the first void volume fraction is loaded into a column having an ion-exchange group opposite to that of the above ion-exchange column (e.g. "TOYOPEARL" (registered trademark) SP-650 manufactured by TOSOH CORPORATION), and a second void volume fraction eluted with distilled water is then collected.

Next, the second void volume fraction is loaded into a gel filtration column (e.g. "SEPHADEX LH-20" (trade name) manufactured by GE Healthcare Japan Corporation), and eluted with a 30 mass % methanol aqueous solution to collect a fraction containing the specific peptide. Finally, using a high-performance liquid chromatography (HPLC) with a reversed-phase column (e.g. "pondasphere 5μ C18 300 Å Column" (trade name) manufactured by Waters Corporation), the fraction is fractionated in accordance with a linear concentration gradient of a 32 mass % or less acetonitrile aqueous solution containing 0.1 mass % trifluoroacetic acid. In this way, the specific peptide can be obtained with a high purity.

<Brain Function Improving Agent or Brain Function Decline Preventing Agent>

The brain function regulating agent according to the present invention is preferably a brain function improving agent or a brain function decline preventing agent. The brain function regulating agent contains a peptide comprising an amino acid sequence represented by Glu-Hyp-Gly, a salt thereof, or a chemically modified product thereof, and can exert a cerebral nerve cell differentiation promoting action by directly acting on cerebral nerve cells as described in [Evaluation Test 1] and [Evaluation Test 2] below. In this way, the brain function regulating agent can produce a brain function improving effect and a brain function decline preventing effect. Therefore, the brain function regulating agent can be used as a brain function improving agent for treatment of a patient whose brain function has declined. The brain function regulating agent can also be used as a brain function decline preventing agent for the purpose of preventing a decline in brain function due to aging or the like.

Preferably, the brain function regulating agent has a cerebral nerve cell differentiation promoting action. Further, it is preferable that the brain function regulating agent have a cerebral nerve cell death suppressive action. It is also preferable that the brain function regulating agent have a memory or cognitive function improving action. The brain function regulating agent can exhibit a cerebral nerve cell differentiation promoting action by directly acting on cerebral nerve cells as described in [Evaluation Test 1] and [Evaluation Test 2] below. From [Evaluation Test 1] and [Evaluation Test 2] described below, the brain function regulating agent can be considered to have a cerebral nerve cell death suppressive action. Through these actions, the brain function regulating agent can exhibit a memory or cognitive function improving action.

The brain function regulating agent can be orally or parenterally administered in various forms. For these forms, the brain function regulating agent can take dosage forms such as tablets, granules, capsules, powders, liquids, suspension preparations and emulsion preparations when orally administered. Further, the brain function regulating agent in any of the above-described dosage forms can be mixed with a food or beverage product.

When parenterally administered, the brain function regulating agent can take dosage forms such as preparations to be injected into the brain, injections, transdermal preparations, suppositories, nasal preparations and inhalations. Preferred dosage forms of the brain function regulating agent include tablets, granules, capsules, powders, and liquids to be directly injected into the brain. The brain function regulating agent contains a tripeptide represented by, for example, Glu-Hyp-Gly, and the tripeptide is rapidly absorbed in the intestinal tract, and therefore can be orally administered.

The dose of the brain function regulating agent varies depending on the age, the sex, the body weight and the sensitivity difference of a subject, the administration method, the administration interval, the type of preparation and the like. When the brain function regulating agent is orally administered, the dose thereof per adult is, for example, preferably 0.0001 to 2,500 mg/kg, more preferably 0.0001 to 500 mg/kg. When the dosage form of the brain function regulating agent is, for example, a tablet, the tablet may contain the brain function regulating agent in an amount of 0.001 to 80 mass % per tablet, and when the dosage form of the brain function regulating agent is, for example, a powder, the powder may contain the brain function regulating agent in an amount of 0.001 to 100 mass %. When the brain function regulating agent is parenterally administered or administered by a preparation in another form, the dose can be appropriately determined by reference to a dose in oral administration. The brain function regulating agent can be administered daily once or in several divided doses, or administered once every day or every several days.

The brain function regulating agent may appropriately contain other active ingredients, a preparation carriers and the like as long as the effects of the present invention are not adversely affected. Examples of other active ingredients include docosahexaenoic acid (DHA), eicosapentaenoic acid (EPA), astaxanthin, ginkgo leaf extracts and arachidonic acid. Further, examples of pharmaceutically acceptable carriers used in formulation into pharmaceutical preparations include diluents, binding agents (syrup, gum arabic, gelatin, sorbitol, tragacanth and polyvinylidone), excipients (lactose, sucrose, cornstarch, potassium phosphate, sorbitol and glycine), lubricants (magnesium stearate, talc, polyethylene glycol and silica), disintegrants (potato starch) and wetting agents (sodium lauryl sulfate).

<Use Invention>

The brain function regulating agent according to the present invention contains a peptide comprising an amino acid sequence represented by Glu-Hyp-Gly, a salt thereof, or a chemically modified product thereof. The brain function regulating agent has a cerebral nerve cell differentiation promoting action as an unknown attribute of a peptide comprising an amino acid sequence represented by Glu-Hyp-Gly, for example a tripeptide represented by Glu-Hyp-Gly, so that at least one of a brain function improving effect and a brain function decline preventing effect can be obtained. In other words, the present invention is a peptide comprising an amino acid sequence represented by Glu-Hyp-Gly, a salt thereof, or chemically modified product thereof for regulation of the brain function.

[Food or Beverage Product]

The food or beverage product according to the present invention contains the brain function regulating agent. For example, a tripeptide represented by Glu-Hyp-Gly, which is preferably contained in the brain function regulating agent, is rapidly absorbed in the intestinal tract, and therefore can be orally administered. Thus, the brain function regulating agent of the present invention can be administered as a food or beverage product in which the brain function regulating agent is mixed with food or a beverage. Further, the food or beverage product according to the present invention can be used as food for specified health uses or food with functional claims. The concentration of the brain function regulating agent contained in the food or beverage product is preferably 0.001 to 100 mass %.

Examples

Hereinafter, the present invention will be described in more detail by way of Example, which should not be construed as limiting the present invention.

[Evaluation Test 1: Clinical Test]

<Test Food Product (Food or Beverage Product Comprising Brain Function Regulating Agent)

As a test food product, a collagen peptide mixture comprising an amino acid sequence represented by Glu-Hyp-Gly ("Collagen Peptide CP-B" (trade name) manufactured by Nitta Gelatin Inc.) was used. During a test period described below, 5 g of the test food product which was added to a beverage was administered to a subject once a day. The administration time of the beverage was not specified.

<Test Design>

The period of the test was four consecutive weeks selected a period from October 20 to Nov. 21, 2016. A comparative test before and after intervention of an open label was conducted in Kokoro Research Center, Kyoto University. In this test, the informed consent procedure was carried out for all of the subjects under the spirit of "Helsinki Declaration" of World Medical Association, and written consents were obtained from all of the subjects. On Sep. 18, 2015, Ethical review Committee of Kyoto University Unit for Advanced Study of Mind approved this test (Approval No. 27-P-13).

In this test, a gray matter volume-brain healthcare quotient (GM-BHQ) score, a fractional anisotropy-brain healthcare quotient (FA-BHQ) score, a mild cognitive impairment (MCI) score and a standard verbal paired associate learning (S-PA) score were obtained to evaluate the effect of the test food product on the brain function.

<Subjects>

In this test, the subjects were 30 healthy persons between 49 and 63 years of age (average age: $56.1\pm3.6$ years old). The major criteria for eligibility of the subjects are as follows: "a person who had not taken a collagen hydrolysate during a month before the start of the test", "a person having no history of major food allergies including gelatin allergy" and "a person having no history of neurological diseases such as brain infarction and dementia, and psychological diseases". In addition, a person falling under the items described in "https://www.acrin.org/Portals/0/Protocols/6684/ACRIN6684_Amend7_012412_master_ForOnline.pdf", Section 6 was excluded from the subjects. During the test period, one subject dropped out for personal reasons. Further, for personal reasons, five subjects did not undergo the test for obtaining the S-PA score. Thus, statistical analyses were performed in accordance with the protocols of the tests on 24 subjects for the test for obtaining the S-PA score and on 29 subjects for the other tests.

<Evaluation Methods and Evaluation Results>

(MRI Scan)

Magnetic resonance image (MRI) scan was performed a day before the start of administration of the test food product (hereinafter, also referred to as "before intervention") and a day after the end of administration of the test food product (day 29 after the start of administration; hereinafter, also referred to as "after intervention"). MRI imaging before intervention was performed between Oct. 20 and Oct. 24, 2016, and MRI imaging after intervention was performed between Nov. 18 and Nov. 21, 2016. The MRI imaging was performed in Kokoro Research Center, Kyoto University. The specific MRI scan method followed the method described in "Nemoto K et al., "MRI-based Brain Health-care Quotients: A bridge between neural and behavioral analyses for keeping the brain healthy", PLoS ONE, 2017, 12(10): e0187137 (https://doi.org/10.1371/journal.pone.0187137)".

As an MRI apparatus, a 3T scanner "Verio" from Siemens AG in Germany was used, and MRI imaging was performed with a 32 channel head array coil. For three-dimensional T1 weighed images, an MP-RAGE pulse sequence was used. The parameters are as follows. Time of repetition (TR): 1,900 ms; Time of echo (TE): 2.52 ms; Time of inversion (TI): 900 ms; Flip angle: 9°; Matrix size: 256×256; Field of view (FOV): 256 mm; Slice thickness: 1 mm. A diffusion tensor image (DTI) was collected by spin echo-echo planar imaging (SE-EPI) using GRAPPA. The slice of the diffusion tensor image was parallel to the OM line.

The parameters are as follows. Time of repetition (TR): 14,100 ms; Time of echo (TE): 81 ms; Flip angle: 90°; Matrix size: 114×114; Field of view (FOV): 224 mm; Slice thickness: 2 mm. A base line image (b=0 s/mm²) and images in 30 diffusion directions with b=1000 s/mm² were obtained.

A gray matter was extracted from the T1 weighed image using SPM 12 which is a brain function mapping tool, and a GM-BHQ score of the whole brain was calculated from a gray matter capacity and a cranial capacity. A fractional anisotropy (FA) image was generated from the diffusion tensor image using FSL 5.0.11 which is software, and on the basis of the FA image, an FA-BHQ score of the whole brain was calculated.

Here, the tool used for statistical analyses performed in the process of calculating the GM-BHQ score and the FA-BHQ score is "STAT Mate III" which is a medical statistical program. For evaluation of significance, within-group comparison before and after intervention was performed on the basis of the Wilcoxon rank-sum test, and it was determined that there was significance when the significance level (P value) was 0.05 or less. Table 1 below shows values before and after intervention, a difference between the values, and a Pvalue (P value) for each of the GM-BHQ score and the FA-BHQ score. In Table 1, the character "N" means the number of subjects, the term "Baseline" means a value before intervention, the term "Post" means a value after intervention, and the sign "Δ" means a difference before and after intervention.

TABLE 1

| | N | Baseline | Post | Δ | P value* (vs. baseline) |
|---|---|---|---|---|---|
| GM-BHQ | 29 | 93.42 ± 5.90 | 93.00 ± 5.92 | −0.42 ± 1.53 | 0.1415 |
| FA-BHQ | 29 | 94.82 ± 4.81 | 95.73 ± 4.46 | 0.91 ± 1.51 | 0.0095 |

*based on the Wilcoxon rank-sum test

As shown in Table 1, a significant improvement in the FA-BHQ score was observed after intervention as compared with the FA-BHQ score before the intervention. There was no significant improvement in the GM-BHQ score. Therefore, the test food product (a collagen peptide mixture containing a tripeptide represented by Glu-Hyp-Gly as a brain function regulating agent) was shown to have a brain function regulating action.

(MCI Score)

The mild cognitive impairment (MCI) score was calculated by using "About MCI Screen (manufactured by Millennia Corporation)" which is a cognitive function checking scale. Specifically, the subject learned 10 words, and the number of words which the subject was able to report vocally after listening to comments unrelated to the test, out of the 10 words, was determined. The test result of each subject was compared with the test results of a group of the same age on the basis of information such as the sex, the age, the number of learning years and the race of the subject, and demographically evaluated in an objective manner to correct the MCI score of each subject. This test was conducted on the same day the MRI scan was performed on each subject.

(S-PA Score)

The standard verbal paired associate learning (S-PA) score was developed by Japan Society for Higher Brain Dysfunction for the purpose of understanding the human's verbal memory. The specific procedure of the test on the S-PA score is as follows. First, a sheet with 10 pairs of related paired words (semantically related words) and 10 pairs of unrelated paired words (semantically hardly-related words) was provided. Next, the 10 pairs of related paired words described on the sheet were vocally read by an examiner, and learned by the subject. Thereafter, the examiner presented one of each of the pairs of paired words, and the subject reported the word paired with the presented word. Further, the 10 pairs of unrelated paired words described on the sheet were vocally read by the examiner, and learned by the subject. Thereafter, the examiner presented one of each of the pairs of paired words, and the subject reported the word paired with the presented word. Finally, the S-PA score of each subject was calculated from the number of words the subject had correctly reported. The 10 pairs of related paired words and 10 pairs of unrelated paired words described on the sheet provided before intervention were different from those described on the sheet provided after intervention. This test was conducted on the same day the MRI scan was performed on each subject.

Here, the "STAT Mate III" was used as a tool also for statistical analyses performed in the process of calculating the MCI score and the S-PA score. For evaluation of significance, within-group comparison before and after intervention was performed on the basis of the Wilcoxon rank-sum test, and it was determined that there was significance when the significance level (P value) was 0.05 or less. Table 2 below shows values before and after intervention, a difference between the values, and a Pvalue (P value) for each of the MCI score and the S-PA score. In Table 2, the character "N" means the number of subjects, the term "Baseline" means a value before intervention, the term "Post" means a value after intervention, and the sign "Δ" means a difference before and after intervention.

TABLE 2

| | N | Baseline | Post | Δ | P value* (vs. baseline) |
|---|---|---|---|---|---|
| MCI score | 29 | 67.83 ± 6.47 | 71.06 ± 6.39 | 3.23 ± 5.79 | 0.0046 |
| S-PA score | 24 | 13.71 ± 6.72 | 19.29 ± 6.63 | 5.58 ± 6.18 | 0.0007 |

*based on the Wilcoxon rank-sum test

As shown in Table 2, a significant improvement in both the MCI score and the S-PA score was observed after intervention as compared with the scores before the invention. When reviewed in light of the results in Table 1, the results in Table 2 indicate that the test food product has a memory or cognitive function improving action through its brain function regulating action, thereby producing a brain function improving effect. Further, the above-described results indicate the test food product also produces a brain function decline preventing effect. Thus, the brain function regulating agent can be used as a brain function improving agent or a brain function decline preventing agent.

(Effect of Brain Function Regulating Agent on Brain Function of Individual Subject)

Whether or not there was a correlation of an increase or decrease in the GM-BHQ score and an increase or decrease in the FA-BHQ score with an increase or decrease in the MCI score and an increase or decrease in the S-PA score in an individual subject was examined to study the effect of the brain function regulating agent on the brain function of the individual subject. For the correlation, the Spearman's rank correlation coefficient (r) was calculated from the measured values, and statistical processing was performed for the values obtained before and after intervention. For the statistical processing, the "STAT Mate III" was used. It was determined that "there was no correlation" when r was 0.2 or less, "there was a low correlation" when r was more than 0.2 and 0.4 or less, "there was a correlation" when r was more than 0.4 and 0.7 or less, "there was a strong correlation" when r was more than 0.7 and less than 1, and "there was a perfect correlation" when r was 1. Table 3 shows values of r which are the results of the evaluation.

TABLE 3

| | N | ΔGM-BHQ | ΔFA-BHQ |
|---|---|---|---|
| ΔMCI | 29 | 0.4448 # | −0.0502 |
| ΔS-PA | 24 | 0.2438 | 0.4645 # |

# P < 0.05, based on the Spearman's rank correlation coefficient (r)

As shown in Table 3, there was a correlation between an increase or decrease in the GM-BHQ score and an increase or decrease in the MCI score, and there was a correlation between an increase or decrease in the FA-BHQ score and an increase or decrease in the S-PA score.

<Discussions>

From the above-described results, it is presumed that the brain function regulating agent comprising a specific peptide has an effect on the brain function of an individual subject such that the brain function regulating agent improves the FA-BHQ score to improve the S-PA score, and improves the GM-BHQ score to improve the MCI score. Thus, the brain function regulating agent can be used as a brain function improving agent or a brain function decline preventing agent.

[Evaluation Test 2: Cell Biological Test (In Vitro Test)]

<Preparation of Sample>

All the animal experiments conformed to "Standard for Rearing and Care of Laboratory Animals" from General Administrative Agency of the Cabinet and "Guideline for Animal Experiments" from Josai University, Life Science Research Center. 15 to 25-week-old male and female Wistar rats were provided by purchase from CREA Japan, Inc. Thereafter, the rats were reared under the following conditions: the temperature was $23\pm2°$ C., the relative humidity was $55\pm10\%$, the lighting cycle was 12 hours, the light period started at 7:00 and ended at 19:00, and the rats were fed with a solid feed ("CE-2" (trade name) manufactured by CREA Japan, Inc) and allowed to freely access drinking water. Under the same conditions as described above, the rats were mated to obtain 7-day-old rats. Further, 3 to 8-day-old Wistar rats were provided by purchase from CREA Japan, Inc.

(Preparation and Culture of Primary-Cultured Cerebellar Granule Cells (CGC))

The Wistar rats were reared to the age of 7 to 9 days under the above-described conditions, and cerebella were then excised from these rats, and dispersed by the below-described method using the dispersion solutions shown in Table 4 (liquids I to V). In this way, dispersions containing granule cells and other cerebral nerve cells (hereinafter, these cells are also referred to collectively as "cerebellar granule cells (CGC)") from the cerebella. The cerebellar granule cells (CGC) are cerebral nerve cells. Thereafter, the CGC contained in the dispersions was cultured. Table 4 shows the "solution names" of the dispersion solutions, the "contained reagents" and the "amounts" thereof. The method for preparing the cerebellar granule cells (CGC) is as follows.

TABLE 4

| Solution name | Contained reagent and amount thereof |
|---|---|
| Liquid I | 10 mL 10 × krebs ringer buffer (35.4 g of NaCl, 18 g of KCl, 0.84 g of $KH_2PO_4$, 10.8 g of $NaHCO_3$, 12.8 g of D-glucose and 50 mg of phenol red were dissolved in 500 mL of Milli-Q water) 90 mL sterile water, 0.8 mL 3.82% $MgSO_4$, 0.3 g BSA |
| Liquid II | 6.25 mg trypsin, 25 mL Liquid I |
| Liquid III | 7.8 mg trypsin inhibitor, 1.2 mg DNase, 0.15 mL 3.82% $MgSO_4$, 15 mL Liquid I |

TABLE 4-continued

| Solution name | Contained reagent and amount thereof |
|---|---|
| Liquid IV | 4 mL Liquid III, 21 mL Liquid I |
| Liquid V | 0.015 mL 1.2% $CaCl_2$, 0.1 mL 3.82% $MgSO_4$, 12.5 mL Liquid I |

First, ten of the 7 to 9-day-old rats were decapitated, and cerebella were excised in the clean bench, and then formed into minced paste with a razor after removal of unnecessary tissues, blood vessels, chorionic membranes and the like. Liquid I was added to the paste to give a suspension, and the suspension was centrifuged at 1,000 rpm for 30 seconds to obtain a first separate liquid containing a supernatant and a cell group. The supernatant was removed from the first separate liquid, liquid II pre-warmed to 37° C. in a thermostatic bath was then added to the remaining cell group little by little, and the mixture was stirred, transferred into a 50 mL medium bottle, and further stirred at 37° C. for 15 minutes to perform tissue digestion with trypsin.

Next, liquid IV was added to the medium bottle to deactivate the trypsin, and the mixture was centrifuged at 1,000 rpm for 30 seconds to obtain a second separate liquid containing a supernatant and a cell group. The supernatant was removed from the second separate liquid, and a small amount of liquid III was then added to the remaining cell group with a Pasteur pipette to disperse the cell group. Thereafter, the mixture was left standing for 15 minutes to obtain a third separate liquid containing a supernatant and a cell group, and the supernatant was taken into liquid V. To the cell group remaining in the third separate liquid, a small amount of liquid III was added to redisperse the cell group. Thereafter, the mixture was left standing for 5 to 10 minutes to obtain a fourth separate liquid containing a supernatant and a cell group, and the supernatant was taken into liquid V containing the supernatant of the third separate liquid.

Liquid V containing the supernatant of the third separate liquid and the supernatant of the fourth separate liquid was centrifuged at 1,000 rpm for 5 minutes to obtain a fifth separate liquid containing a supernatant and a cell group. The supernatant was removed from the fifth separate liquid, a basal medium (BME: Basal Medium Eagle manufactured by Sigma-Aldrich Co. LLC) was then added to the remaining cell group, and the mixture was stirred to obtain a mixed liquid containing cerebellar granule cells (CGC) and BME. Thereafter, the mixed liquid was stained with a trypan Blue solution with a concentration of 0.4 mass %, and the number of the stained cells and the viability thereof were measured.

Next, K+5 mM serum (+) BME was added to the mixed liquid in such a manner that the cell density of living cells was $1.2\times10^5$ cells/mL, and the mixture was suspended to obtain a culture sample. The culture sample was seeded at 0.766 mL per well in a 12-well plate pre-coated with poly-L-lysin (PLL) with a concentration of 50 μg/mL, and was cultured in an incubator environment of $CO_2$ with a concentration of 5 vol % at 37° C. ("on day 0 after the start of culture").

On day 1 after the start of culture, to each well was added cytosine β-D-arabinofuranoside (AraC) to a final concentration of 10 μM for the purpose of suppressing growth of non-neuronal cells while maintaining only CGC. Further, in the below-described control sample, KCl was added to a final concentration of 25 mM. In other samples (samples containing the peptides or amino acids shown in Tables 5 to 7 below), KCl was added with an adjustment made to a final concentration of 15 mM.

Further, on days 1 and 4 after the start of culture, the peptides or amino acids shown in Tables 5 to 7 were added to the final concentrations shown in Tables 5 to 7, respectively, to prepare samples.

On day 7 after the start of culture, the viability of CGC was measured by an MTT assay method to examine whether or not each of the samples had a differentiation promoting action on CGC. Specifically, the percent ratio of the number of living cells in each sample to the number of living cells in the control sample having a KCl concentration of 25 mM was determined, and subjected to statistical processing to evaluate significance of the differentiation promoting action on CGC. The evaluation of significance, statistical processing was performed using software ("BellCurve for Excel (Ver 2.1)" (trade name) manufactured by Social Survey Research Information Co., Ltd.), Smirnov-Grubbs (two-sided test) was conducted, and the significance level (P value) was set to 0.05 for refusal. Thereafter, the Student's t-test (t-test) was conducted to evaluate significance. Tables 5 to 7 show the results. Samples with "* (asterisk)" in Tables 5 to 7 were determined to have a differentiation promoting action on CGC (have a significance).

Here, in Table 5, "control (K+)" means a control sample. "NMDA" ("M3262" (trade name) manufactured by Sigma-Aldrich Co. LLC) means a sample containing N-methyl-D-aspartic acid, and "BDNF" ("SRP3014" (trade name) manufactured by Sigma-Aldrich Co. LLC) means a sample containing a brain-derived neurotrophic factor. "NMDA" and "BDNF" are known to be involved in differentiation of cerebral nerve cells, and are each used as Reference Example in this test.

Further, for the peptides shown in Tables 5 to 7, an abbreviation is used in which an amino acid is represented by one character. C represents a cyclic structure, H represents histidine, P represents proline, G represents glycine, O represents hydroxyproline, E represents glutamic acid, and A represents alanine. That is, in Table 5, "C-HP" means a sample containing a cyclic dipeptide consisting of histidine-proline (manufactured by PH Japan Co., Ltd.), "C-GP" means a sample containing a cyclic dipeptide consisting of glycine-proline (manufactured by PH Japan Co., Ltd.), and "TRH" means a sample containing a thyrotropin-releasing hormone (manufactured by PH Japan Co., Ltd.). These samples are known to pass through a blood-brain barrier, and are each used as Comparative Example. In Table 5, "Glutamic acid" means a sample containing glutamic acid known to have an antioxidant action ("G1251" (trade name) manufactured by Sigma-Aldrich Co. LLC). "Glutathione" means a sample containing glutathione similar in chemical structure to Glu-Hyp-Gly (EOG) ("G6013" (trade name) manufactured by Sigma-Aldrich Co. LLC). "GPO" means a sample containing a tripeptide consisting of glycine-proline-hydroxyproline (manufactured by PH Japan Co., Ltd.). "Glutamic acid", "glutathione" and "GPO" are each used as Comparative Example.

In Table 6, "C-PO" means a sample containing a cyclic dipeptide consisting of proline-hydroxyproline (manufactured by PH Japan Co., Ltd.), "C-OG" means a sample containing a cyclic dipeptide consisting of hydroxyproline-glycine (manufactured by PH Japan Co., Ltd.), and "C-EO" means a sample containing a cyclic dipeptide consisting of glutamic acid-hydroxyproline (manufactured by PH Japan Co., Ltd.). In Table 6, "PO" means a sample containing a dipeptide consisting of proline-hydroxyproline ("G-3025

(trade name) manufactured by BACHEM Co.), "OG" means a sample containing a dipeptide consisting of hydroxyproline-glycine ("G-2365" (trade name) manufactured by BACHEM Co.), and "AO" means a sample containing a dipeptide consisting of alanine-hydroxyproline (manufactured by PH Japan Co., Ltd.). "PO" is known to pass through a blood-brain barrier. "C-PO", "C-OG", "C-EO", "PO", "OG" and "AO" are each used as Comparative Example.

In Table 7, "GP" means a sample containing a dipeptide consisting of glycine-proline ("G-3015" (trade name) manufactured by BACHEM Co.), and "EO" means a sample containing a dipeptide consisting of glutamic acid-hydroxyproline (manufactured by PH Japan Co., Ltd.). "GP" and "EO" are each used as Comparative Example. "EOG" means a sample containing a tripeptide represented by Glu-Hyp-Gly (manufactured by PH Japan Co., Ltd.), and is used as Example in this test.

TABLE 5

| Amino acid or peptide | Content (concentration) | Viability (%) | Significant difference |
|---|---|---|---|
| Control (K+) | 25 mM | 100 | — |
| NMDA | 0 µM | 64.4 | — |
| | 100 µM | 93.4 | * |
| BDNF | 0 ng/mL | 61.2 | — |
| | 100 ng/mL | 76.6 | * |
| IGF-1 | 0 ng/mL | 64.8 | — |
| | 100 ng/mL | 67.1 | — |
| Glutamic acid | 0 µM | 52.5 | — |
| | 10 µM | 58.1 | — |
| | 100 µM | 52.4 | — |
| | 1000 µM | 42.4 | — |
| C-HP | 0 µM | 62.3 | — |
| | 10 µM | 65.1 | — |
| | 100 µM | 63.9 | — |
| | 1000 µM | 69.2 | — |
| C-GP | 0 µM | 47.2 | — |
| | 10 µM | 51.2 | — |
| | 100 µM | 46.4 | — |
| | 1000 µM | 53.3 | — |
| TRH | 0 µM | 49.4 | — |
| | 10 µM | 59.3 | — |
| | 100 µM | 52 | — |
| | 1000 µM | 60.1 | — |
| Glutathione | 0 µM | 65.7 | — |
| | 0.01 µM | 73.9 | — |
| | 0.1 µM | 63.5 | — |
| | 1 µM | 63.5 | — |
| | 10 µM | 63.6 | — |
| | 100 µM | 60.0 | — |
| | 1000 µM | 67.1 | — |
| GPO | 0 µM | 54.3 | — |
| | 0.1 µM | 56.3 | — |
| | 1 µM | 58.4 | — |
| | 10 µM | 59.0 | — |
| | 100 µM | 55.8 | — |
| | 1000 µM | 61.5 | — |

TABLE 6

| Amino acid or peptide | Content (concentration) | Viability (%) | Significant difference |
|---|---|---|---|
| C-PO | 0 µM | 72.3 | — |
| | 0.1 µM | 55.7 | — |
| | 1 µM | 58.4 | — |
| | 10 µM | 73.2 | — |
| | 100 µM | 70.6 | — |
| | 1000 µM | 68.4 | — |
| C-OG | 0 µM | 54.3 | — |
| | 0.1 µM | 57.8 | — |
| | 1 µM | 63.2 | — |
| | 10 µM | 54.2 | — |

TABLE 6-continued

| Amino acid or peptide | Content (concentration) | Viability (%) | Significant difference |
|---|---|---|---|
| | 100 μM | 50.1 | — |
| | 1000 μM | 62.7 | — |
| C-EO | 0 μM | 63.2 | — |
| | 0.1 μM | 51.3 | — |
| | 1 μM | 52.0 | — |
| | 10 μM | 64.8 | — |
| | 100 μM | 65.0 | — |
| | 1000 μM | 69.3 | — |
| PO | 0 μM | 69.6 | — |
| | 0.1 μM | 52.6 | — |
| | 1 μM | 51.8 | — |
| | 10 μM | 76.3 | — |
| | 100 μM | 72.9 | — |
| | 1000 μM | 74.0 | — |
| OG | 0 μM | 74.5 | — |
| | 0.1 μM | 54.5 | — |
| | 1 μM | 61.8 | — |
| | 10 μM | 77.6 | — |
| | 100 μM | 72.8 | — |
| | 1000 μM | 71.1 | — |
| AO | 0 μM | 68.4 | — |
| | 0.1 μM | 55.1 | — |
| | 1 μM | 57.0 | — |
| | 10 μM | 66.1 | — |
| | 100 μM | 64.7 | — |
| | 1000 μM | 65.9 | — |

TABLE 7

| Amino acid or peptide | Content (concentration) | Viability (%) | Significant difference |
|---|---|---|---|
| GP | 0 μM | 57.5 | — |
| | 0.1 μM | 48.4 | — |
| | 1 μM | 61.2 | — |
| | 10 μM | 65.7 | — |
| | 100 μM | 63.4 | — |
| | 1000 μM | 72.2 | — |
| EO | 0 μM | 78.2 | — |
| | 0.1 μM | 52.9 | — |
| | 1 μM | 54.8 | — |
| | 10 μM | 86.8 | — |
| | 100 μM | 81.2 | — |
| | 1000 μM | 86.7 | — |
| EOG | 0 μM | 64.4 | — |
| | 0.1 μM | 69.9 | — |
| | 1 μM | 69.7 | — |
| | 10 μM | 76.6 | * |
| | 100 μM | 74.4 | * |
| | 1000 μM | 77.7 | * |

<Discussions>

From Tables 5 to 7, it is apparent that as in the case of Reference Examples in which NMDA and BDNF were added, EOG had an action of promoting differentiation of CGC by directly acting on CGC. Tables 5 to 7 indicate that EOG had a CGC death suppressive action.

<Discussions Drawn from Evaluation Tests 1 and 2>

Evaluation tests 1 and 2 show that the brain function regulating agent according to the present invention and a food or beverage containing the brain function regulating agent can promote differentiation of cerebral nerve cells by directly acting on the cerebral nerve cells. Through such an action, the brain function regulating agent and the food or beverage containing the brain function regulating agent can exhibit a memory or brain function improving action. Thus, the brain function regulating agent can be used as a brain function improving agent or a brain function decline preventing agent.

[Evaluation Test 3: In Vitro Test for Analyzing Effective Concentration of EOG]

The effective concentration of EOG, which enabled exhibition of a differentiation promoting action on CGC, was examined by using the same method as in evaluation test 2 except that on days 1 and 4 after the start of culture, EOG was added to final concentrations shown in Table 8. Table 8 shows the results.

TABLE 8

| Amino acid or peptide | Content (concentration) | Viability (%) | Significant difference |
|---|---|---|---|
| EOG | 0 μM | 59.2 | — |
| | 1 μM | 63.7 | — |
| | 3 μM | 67.2 | — |
| | 7 μM | 72.7 | * |
| | 10 μM | 76.1 | * |

<Discussions>

As shown in Table 8, EOG can exhibit a significant differentiation promoting action on CGC when the concentration of EOG is 7 μM or more.

[Evaluation Test 4: Evaluation Test for Analyzing Deliverability of Orally Administered EOG to Cerebral Parenchyma]

<Preparation of Sample>

All the experimental animals were treated in accordance with "Standard for Breeding and Care of Laboratory Animals" from General Administrative Agency of the Cabinet. Two 8-week-old ddy male mice were purchased from Sankyo Labo Service Corporation, Inc. Thereafter, the male mice were acclimated for 1 week to grow to 9-week-old male mice, and then fasted for 12 hours. Subsequently, 250 μL of an aqueous solution containing 20 mg of EOG (Glu-Hyp-Gly, manufactured by PH Japan Co., Ltd., purity: 95% or more) was orally administered to the male mice enforcedly to prepare two male mice to be used for analyzing deliverability of EOG to the cerebral parenchyma.

An anesthetic was subcutaneously injected into the male mice before oral administration (0 hour), and 10 minutes before each of elapse of 1 hour, elapse of 2 hours and elapse of 4 hours after oral administration. The anesthetic is called a triple anesthetic combination, and contains medetomidine hydrochloride in an amount of 0.3 mg/kg, midazolam in an amount of 4 mg/kg and butorphanol tartrate in an amount of 4 mg/kg. 10 minutes after the injection of the anesthetic, from each of the male mice, 0.5 to 7 μL of cerebrospinal fluid was taken, 20 to 80 μL of blood was taken from the tail vain, and 0.28 to 0.33 mg of part of the cerebral parenchyma (hereinafter, also referred to simply as a "brain") was excited.

The blood was first centrifuged at a centrifugal acceleration of 20,400 G at 4° C. for 10 minutes to obtain plasma, and the plasma was temporarily stored at –80° C. Subsequently, the plasma was mixed with three times its volume of ethanol, and the mixture was then centrifuged at a centrifugal acceleration of 1,000 G at 4° C. for 10 minutes to obtain a supernatant. Thereafter, ammonium bicarbonate prepared to 50 mM was added to the supernatant in an amount four times the volume of the supernatant, followed by mixing. Further, the supernatant containing the ammonium bicarbonate was filtered with a 0.2 μm filter (manufactured by Sartorius AG) to obtain samples to be used for measuring the amount of EOG in the plasma of the male mice (samples before oral administration (0 hour) and after elapse of 1 hour, after elapse of 2 hours and after elapse of 4 hours after oral administration; hereinafter, these samples are also referred to collectively as a "sample a").

The cerebrospinal fluid was mixed with three times its volume of ethanol, and the mixture was then centrifuged at a centrifugal acceleration of 1,000 G at 4° C. for 10 minutes. Thereafter, ammonium bicarbonate prepared to 50 mM was added to the centrifuged cerebrospinal fluid in an amount of 50 μL, and the mixture was stirred. Further, the cerebrospinal fluid containing the ammonium bicarbonate was filtered with a 0.2 μm filter (manufactured by Sartorius AG) to obtain samples to be used for measuring the amount of EOG in the cerebrospinal fluid of the male mice (samples before oral administration (0 hour) and after elapse of 1 hour, after elapse of 2 hours and after elapse of 4 hours after oral administration; hereinafter, these samples are also referred to collectively as a "sample b").

The brain was washed with PBS (phosphate buffered physiological saline), then wrapped in aluminum foil, then frozen in liquid nitrogen, and then stored in a frozen state in a freezer (−80° C.). Thereafter, the brain was thawed, homogenized with PBS equal in amount to the brain, and mixed with acetonitrile in an amount three times the weight of the brain, and the mixture was then centrifuged at a centrifugal acceleration of 1,000 G at 4° C. for 10 minutes to obtain a suspension. Subsequently, ammonium bicarbonate prepared to 50 mM was added to the suspension in an amount twice the volume of the suspension, followed by mixing. Further, the suspension containing the ammonium bicarbonate was filtered with a 0.2 μm filter (manufactured by Sartorius AG) to obtain samples to be used for measuring the amount of EOG in the brain (samples before oral administration (0 hour) and after elapse of 1 hour, after elapse of 2 hours and after elapse of 4 hours after oral administration; hereinafter, these samples are also referred to collectively as a "sample c").

The amounts of EOG in samples a, b and c were quantitatively analyzed by LC-MS/MS under conditions described below. Since the samples were appropriately diluted, correction was made by the following calculation equation to determine actual amounts of EOG.

$$\text{Actual amount of EOG (μM)} = \text{analytical value (nM)} \times \text{dilution conversion factor}/1000 \text{ (unit conversion)}$$

Figure 2:
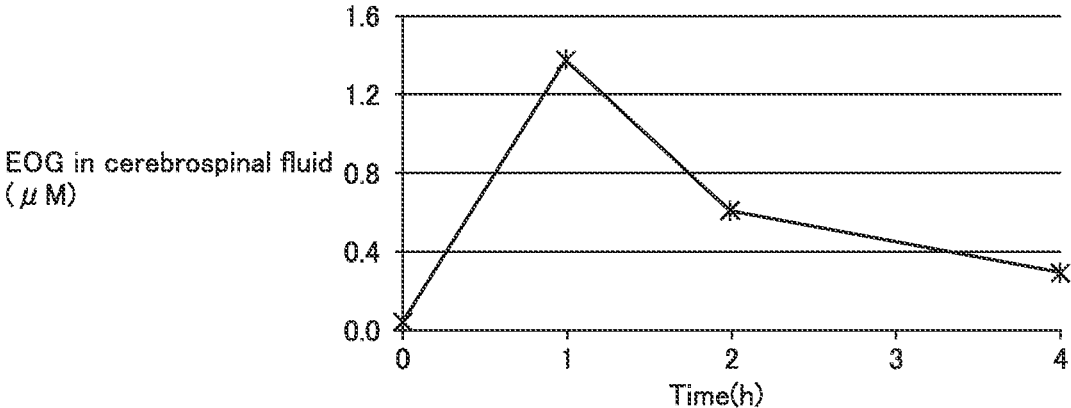
FIG. 2 is a graph showing the amount of EOG in the cerebrospinal fluid (sample b) of male mice after the elapse of a predetermined period of time after gavage administration of EOG to the male mice.
Figure 3:
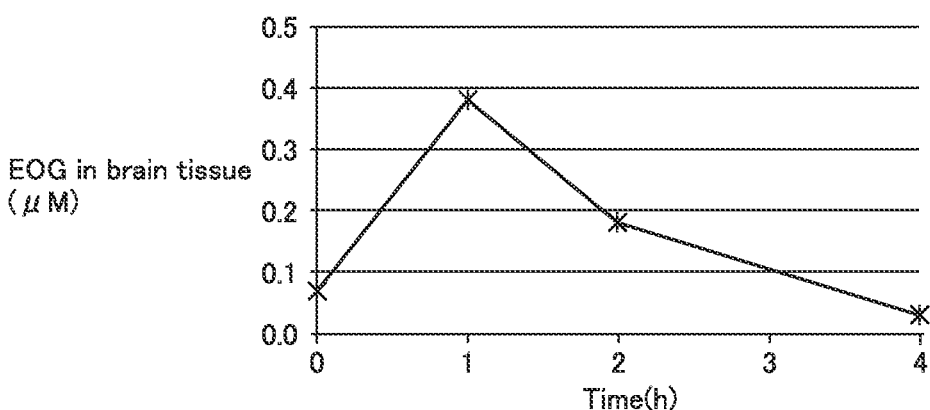
FIG. 3 is a graph showing the amount of EOG in the brain (sample c) of male mice after the elapse of a predetermined period of time after gavage administration of EOG to the male mice.

FIGS. 1, 2 and 3 show the results. FIG. 1 is a graph showing the amount of EOG in the plasma (sample a) of male mice after the elapse of a predetermined period of time after enforced oral administration of EOG to the male mice. FIG. 2 is a graph showing the amount of EOG in the cerebrospinal fluid (sample b) of male mice after the elapse of a predetermined period of time after enforced oral administration of EOG to the male mice. FIG. 3 is a graph showing the amount of EOG in the brain (sample c) of male mice after the elapse of a predetermined period of time after enforced oral administration of EOG to the male mice. The amount of EOG shown in each of FIGS. 1 to 3 is an average value for two male mice.

The quantitative analysis by LC-MS/MS was performed under the following conditions.

HPLC apparatus: ACQUITY UPLC H-Class Bio (manufactured by Waters Corporation)

Column: Hypersil GOLD PFP 2.1×150 mm, 5 μm (manufactured by Thermo Fisher Scientific. Inc.)

Column temperature: 40° C. (linear gradient)

Mobile phase:
(A) aqueous solution containing 0.2% formic acid and 2 mM ammonium acetate
(B) 100% methanol
(Gradient Setting)

| Time (min) | Flow rate | Mobile phase (mass %) |
| --- | --- | --- |
| Initial | 200 | 98 |
| 3.50 | 200 | 98 |
| 3.51 | 400 | 5 |
| 7.00 | 400 | 5 |
| 7.10 | 200 | 98 |
| 17.00 | 200 | 98 |

Injection amount: 0.5 μl

MS/MS Apparatus: "Xevo TQ-XS" manufactured by Waters Corporation

Ionization method: Positive ESI

Capillary (kV): 1

Desolvation temperature (° C.): 500

Source temperature (° C.): 150

MRM Conditions:

| Peptide (abbreviation) | precursor ion (m/z) | product ion (m/z) |
| --- | --- | --- |
| Glu-Hyp-Gly (EOG) | 318 | 225 |

<Discussions>

From FIGS. 1 to 3, it is understood that EOG orally administered to the male mice enforcedly is transferred into the blood, and then into the cerebrospinal fluid. It is understood that the EOG transferred into the cerebrospinal fluid is also transferred to brain tissues in a short time of about 1 hour after oral administration. This indicates that orally administered EOG is transferred via the blood, and thus part of the EOG is delivered to brain tissues through the cerebrospinal fluid.

While embodiments and Examples of the present invention have been described above, the configurations of the embodiments and Examples described above may be appropriately combined as originally envisioned.

The embodiments and Examples disclosed herein should be regarded as illustrative rather than limiting in any way. The scope of the present invention is given by the appended claims rather than the foregoing description, and all changes which fall within the range of the appended claims and equivalents thereof are intended to be embraced therein.

The invention claimed is:

1. A method for suppressing cerebellar granule cell death in a patient in need thereof, comprising administering to the patient in need thereof a cerebellar granule cell death suppressing effective amount of a tripeptide consisting of the amino acid sequence of Glu-Hyp-Gly, a salt thereof, or a composition comprising the tripeptide or a salt thereof;

wherein the effective amount is an amount sufficient to deliver to cerebellar granule cells the tripeptide or a salt thereof at a concentration in a cerebrospinal fluid of 7 μM or more.

2. The method according to claim 1, wherein the tripeptide is derived from collagen.

* * * * *